(12) United States Patent  (10) Patent No.: US 7,581,425 B2
Forrest  (45) Date of Patent: Sep. 1, 2009

(54) GAS SENSOR CALIBRATION SYSTEM

(75) Inventor: Steven Gerard Forrest, Poole (GB)

(73) Assignee: Honeywell Analytics Limited, Bracknell, Berkshire (GB)

( * ) Notice: Subject to any disclaimer, the term of this patent is extended or adjusted under 35 U.S.C. 154(b) by 0 days.

(21) Appl. No.: 11/553,074

(22) Filed: Oct. 26, 2006

(65) Prior Publication Data
US 2007/0044534 A1 Mar. 1, 2007

Related U.S. Application Data

(62) Division of application No. 10/450,311, filed as application No. PCT/GB01/05472 on Dec. 11, 2001, now Pat. No. 7,146,841.

(30) Foreign Application Priority Data
Dec. 11, 2000 (GB) ................. 0030167.1

(51) Int. Cl.
G01N 37/00 (2006.01)
(52) U.S. Cl. ...................................... 73/1.06
(58) Field of Classification Search .......... 73/1.06–1.07
See application file for complete search history.

(56) References Cited
U.S. PATENT DOCUMENTS

| | | | | |
|---|---|---|---|---|
| 4,151,738 A | * | 5/1979 | Hyer et al. ................. | 73/23.21 |
| 4,462,244 A | | 7/1984 | Lee | |
| 4,481,804 A | * | 11/1984 | Eberhard et al. ............. | 73/1.06 |
| 4,489,590 A | | 12/1984 | Hadden | |
| 4,854,153 A | | 8/1989 | Miyagawa et al. | |
| 5,239,492 A | * | 8/1993 | Hartwig et al. ............... | 73/1.07 |
| 5,332,547 A | * | 7/1994 | Olson et al. ..................... | 422/3 |
| 5,355,781 A | * | 10/1994 | Liston et al. .................. | 99/476 |
| 5,402,665 A | * | 4/1995 | Hart et al. ..................... | 73/1.06 |
| 5,665,894 A | | 9/1997 | Baker | |
| 5,667,651 A | * | 9/1997 | Bryan ......................... | 204/401 |
| 5,761,952 A | * | 6/1998 | Gilby et al. .................. | 73/1.06 |
| 6,475,158 B1 | * | 11/2002 | Orr et al. ..................... | 600/531 |
| 6,632,674 B1 | * | 10/2003 | Warburton ..................... | 436/8 |

FOREIGN PATENT DOCUMENTS

| | | |
|---|---|---|
| GB | 392 727 A | 10/2004 |
| JP | H05-008775 | 2/1993 |
| WO | WO 01/86286 | 11/2001 |

OTHER PUBLICATIONS

Patent Abstracts of Japan, Publication No. 61000737, Jan. 6, 1986 (Shimadzu Corp.); "Automatic Calibration Gas Introduction Time Decision Mechanism For Continuous Analyzer".
Office Action from Japanese Patent Office for corresponding Japanese Patent Application No. 2002-549961, mailing date: Sep. 25, 2007.

* cited by examiner

Primary Examiner—Hezron Williams
Assistant Examiner—Nashmiya S Fayyaz
(74) Attorney, Agent, or Firm—Husch Blackwell Sanders Welsh & Katz

(57) ABSTRACT

A portable detector is described for monitoring a gas in an atmosphere. The detector comprises a housing, at least one gas sensor carried by the housing, and electrical connectors carried by the housing for establishing electrical connections to a calibration apparatus and a microprocessor carried by the housing. The microprocessor controls the calibration apparatus via signals provided to microprocessor through the connectors to initiate the supply of calibration gas to the detector at a predetermined rate.

9 Claims, 6 Drawing Sheets

GAS SENSOR CALIBRATION SYSTEM

CROSS-REFERENCE TO RELATED APPLICATION

This application is a Divisional application of U.S. Ser. No. 10/450,311 filed Nov. 18, 2003 entitled "Gas Sensor Calibration System", which is incorporated herein by reference, and which claims the benefit of the filing date of International Application No. PCT/GB 01/05472 with International filing date Dec. 11, 2001 which claims the benefit of GB 0030167.1 filed Dec. 11, 2000.

FIELD OF INVENTION

The present invention relates to a system for calibrating gas sensors, which are used in gas detection instruments and gas analyzers (the term "detector" will be used in this specification to cover both types of apparatus) to detect or analyse potentially hazardous environments to ensure that the sensors provide accurate readings.

BACKGROUND

Portable gas detectors containing electrochemical gas sensors are well-known for monitoring potentially hazardous environments, for example mines, tunnels, sewers and other closed environments. Such detectors are generally of the type in which gas from the atmosphere comes into contact with the sensors(s) within the detector by diffusion. Electronic circuits within the detector convert the output signal from each sensor into a reading of the amount of gas detected. The sensor output per unit amount of gas can vary with time and hence periodic calibration is required to ensure that the detector reading is accurate. Safety regulations require that the sensors within the detector are tested on each occasion that they are taken into a potentially hazardous environment and calibrated according to manufacturer's recommendations and that is indeed good commercial practice but it is frequently not complied with for reasons of cost and time.

Currently, sensors within such detectors are calibrated by passing a calibration gas of known fixed composition by passing a calibration gas of known fixed composition from a compressed gas bottle at a predetermined flow rate through a loose pipeline to a hood clipped onto the detector. The calibration gas entering the detector displaces ambient air within the detector so that the environment that the sensor is exposed to is composed wholly of calibration gas. Excess calibration gas flows out of the hood and is vented to atmosphere and so the procedure is wasteful of calibration gas, which is expensive. In addition, the gas required for calibration could be hazardous and if substantial quantities are vented, calibration should be carried out in a controlled environment. Typically a high flow rate of about 0.5 liters/minute are used since a lower rate is prone to error resulting from drafts and incorrect setting of the valves controlling the flow of gas.

The calibration gas is allowed to flow until the sensor output has reached a steady state. Since the calibration gas has a known composition, the gain of the circuits within the detector that convert the output signal from each sensor into a reading of the amount of gas detected can be adjusted to provide the correct reading.

The known calibration procedures are not straightforward and the correct setting of the valves to achieve the correct gas flow rates and the adjustment of the settings in the detectors is a skilled job requiring training and so calibration has hitherto been performed only periodically, typically every 3 to 6 months by sending the detectors to the original manufacturer or appointed service agent. This requires a stock of spare detectors to be held, or an expensive site visit to perform the calibration. For these reasons calibration has been expensive and consequently is often not performed as frequently as the regulations require.

U.S. Pat. No. 4,854,153 describes an automatic gas sensor calibration apparatus that exposes the sensor to two different concentrations of gas to perform the calibration. If a fault is detected in the gas supply, calibration is prematurely terminated to save calibration time. The calibration apparatus totally controls the calibration measurements according to a regime that is pre-set by the apparatus and the calibration values measured are stored within a memory in the apparatus.

U.S. Pat. No. 5,655,894 describes a gas sensor calibration system wherein gas is drawn into the calibration system by a pump, where it is metered out by a piston-cylinder arrangement.

The present invention provides an alternative, quicker and more cost effective method of calibrating gas sensors that can be performed quickly on site with minimal training. This makes it practically and economically feasible for the personnel entering a hazardous environment to perform a calibration on each occasion that they enter such an environment, thereby increasing safety.

DISCLOSURE OF INVENTION

According to the present invention, there is provided an apparatus for calibrating at least one sensor within a gas detector, which detector has a gas inlet in fluid communication with each sensor, the apparatus comprising a housing that contains:

a) a surface for abutting against a detector;

b) a holder for holding a gas detector with respect to the housing in such a manner that a region of the detector containing the gas inlet abuts against the surface of the housing to form a sealed gas interface between the surface and the detector;

c) a connector for connecting a source of pressurized calibration gas to the apparatus, d) a conduit for delivering a calibration gas from the connector to the interface between the detector and the apparatus housing, e) electrical connectors within the holder for forming electrical connections between the apparatus and a detector held within the holder, and f) a flow controller within the conduit for providing calibration gas at a predetermined level to the interface, the flow controller including an electrically-operated valve being controllable for initiating and terminating the flow of calibration gas through the conduit by means of signals received from the detector via the electrical connections.

Because all the components necessary to perform calibration are all supplied within a single housing, the distance between the pressurized calibration gas connector and the surface for abutting against the detector can be kept to a minimum, e.g. less than 10 cms, more preferably less than 5 cms, so that the amount of gas space within the apparatus that must be flushed with calibration gas is kept to a minimum to save calibration gas and to speed up calibration.

The detector preferably includes a calibration circuit for calibrating automatically the output of the detector to accord with the composition of the calibration gas.

The apparatus and the detector each includes electrical connectors for forming electrical connections between the detector and the apparatus whereby the operation of the calibration apparatus, e.g. the flow of calibration gas to the detector, can be controlled in accordance with instructions held within the detector. To that end, the apparatus includes an electronically controllable valve for initiating and terminating the flow of calibration gas through the conduit in accordance with signals received from the detector. In this way the calibration can be performed automatically with sufficient calibration gas being supplied for the signal from the sensor (s) within the detector to reach a steady state. Since calibration is wholly under the control of the detector, there is no need for specialized staff (or indeed any staff) to perform calibration.

The surface against which the detector abuts is preferably surrounded by a compliant seal to form a gas-impervious seal around the interface between the detector and the housing.

A detector may be pressed against the surface of the housing by a spring biased arm, or some other mechanical arrangement that urges the detector against the calibration apparatus.

The present invention also provides a method of calibrating at least one sensor within a gas detector that has a gas inlet in fluid communication with each sensor, the method using an apparatus comprising a housing that contains:

a) a surface for abutting against a detector to form a sealed gas interface between the surface and the detector, b) a source of pressurized calibration gas containing a known concentration of gases that the at least one sensor is responsive to, and c) a conduit for delivering the calibration gas to the interface between the detector and the housing, the method comprising:

i. urging a gas detector against the surface of the housing such that the region of the detector containing the gas inlet abuts against the surface of the housing, ii. allowing calibration gas to flow from the source to the sealed gas interface at a predetermined rate, and iii. calibrating the at least one sensor within the detector such that the detector provides a reading corresponding to the known concentration of gases within the calibration gas, wherein the detector initiates the flow of calibration gas to the sealed gas interface, automatically calibrates the at least one sensor within the detector and stops the flow of calibration gas following calibration.

According to this method, the detector may initiate the flow of calibration gas, automatically calibrate the at least one sensor within the detector and stop the flow of calibration gas following calibration.

The detector advantageously generates an error signal if the calibration process is not completed within a predetermined time, e.g. 1 minute, or if the signal from the at least one sensor during calibration falls outside a predetermined range.

The present invention also provides a detector.

By reducing the volume of gas space between the source of pressurized calibration gas and the detector and by forming a gas tight seal between the calibration apparatus and a detector, the predetermined flow rate of calibration gas can be as low as 0.1 liters/minute +−20% and permits the sensor(s) to come to an equilibrium value quickly which reduces the consumption of expensive calibration gas. Also, because the detector can stop the flow of calibration gas immediately after it detects the sensor output(s) have reached a steady state, less calibration gas is required for each calibration.

By including the connection to the gas cylinder and the outlet to the sensor within a single housing of the calibrating apparatus, it is possible to reduce the length of the gas path between the source of calibration gas and the sensor itself, which in turn means that the sensor calibration can be done more quickly than hitherto and because the calibration is controlled by the detector, there is no need for expensive personnel to perform calibration.

BRIEF DESCRIPTION OF THE DRAWINGS

A calibration apparatus according to the present invention will now be described by way of example with reference to the drawings in which.

DETAILED DESCRIPTION

Figure 1:
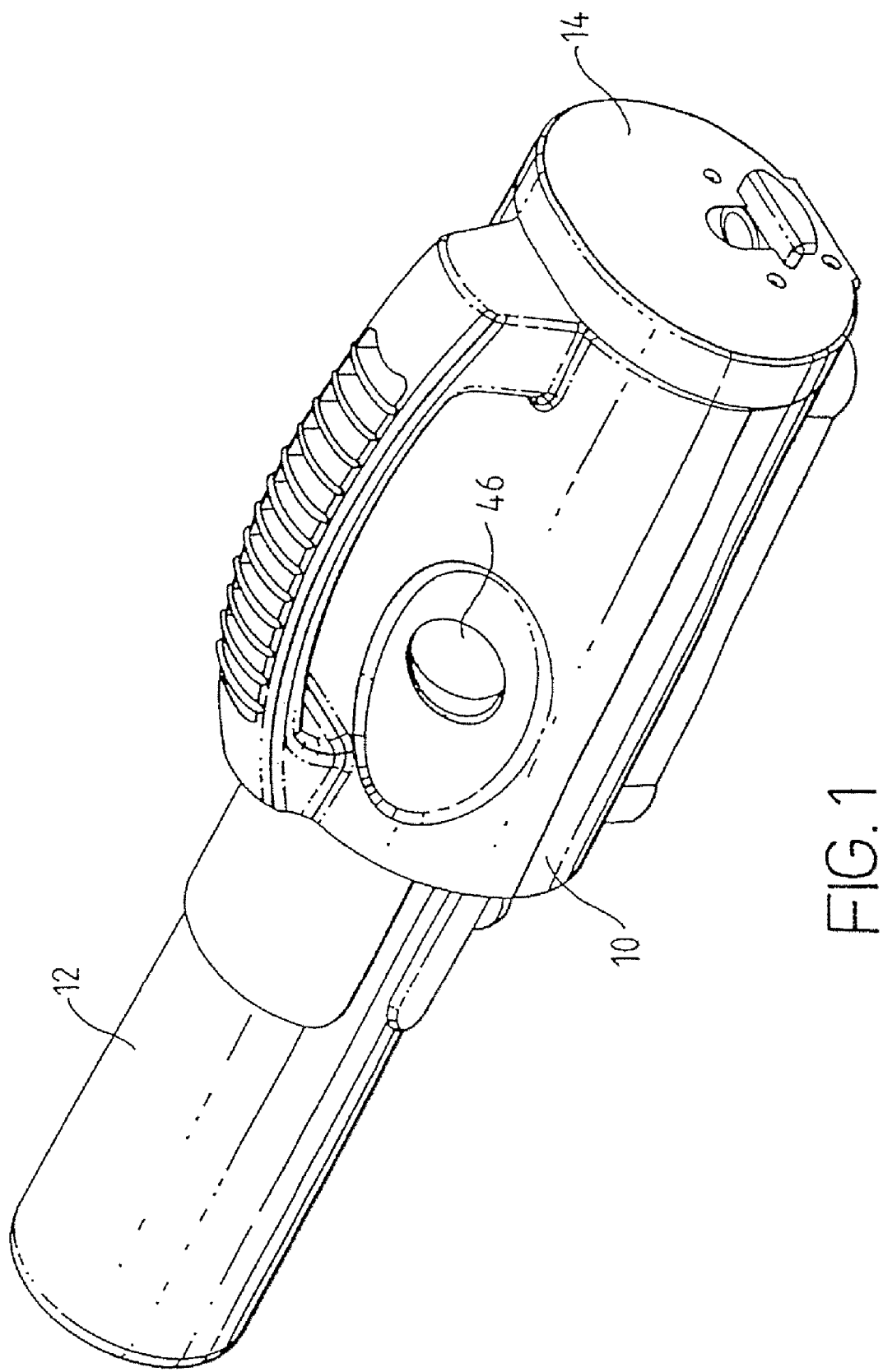
FIG. 1 is a perspective view of a calibration apparatus according to the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Figure 2:
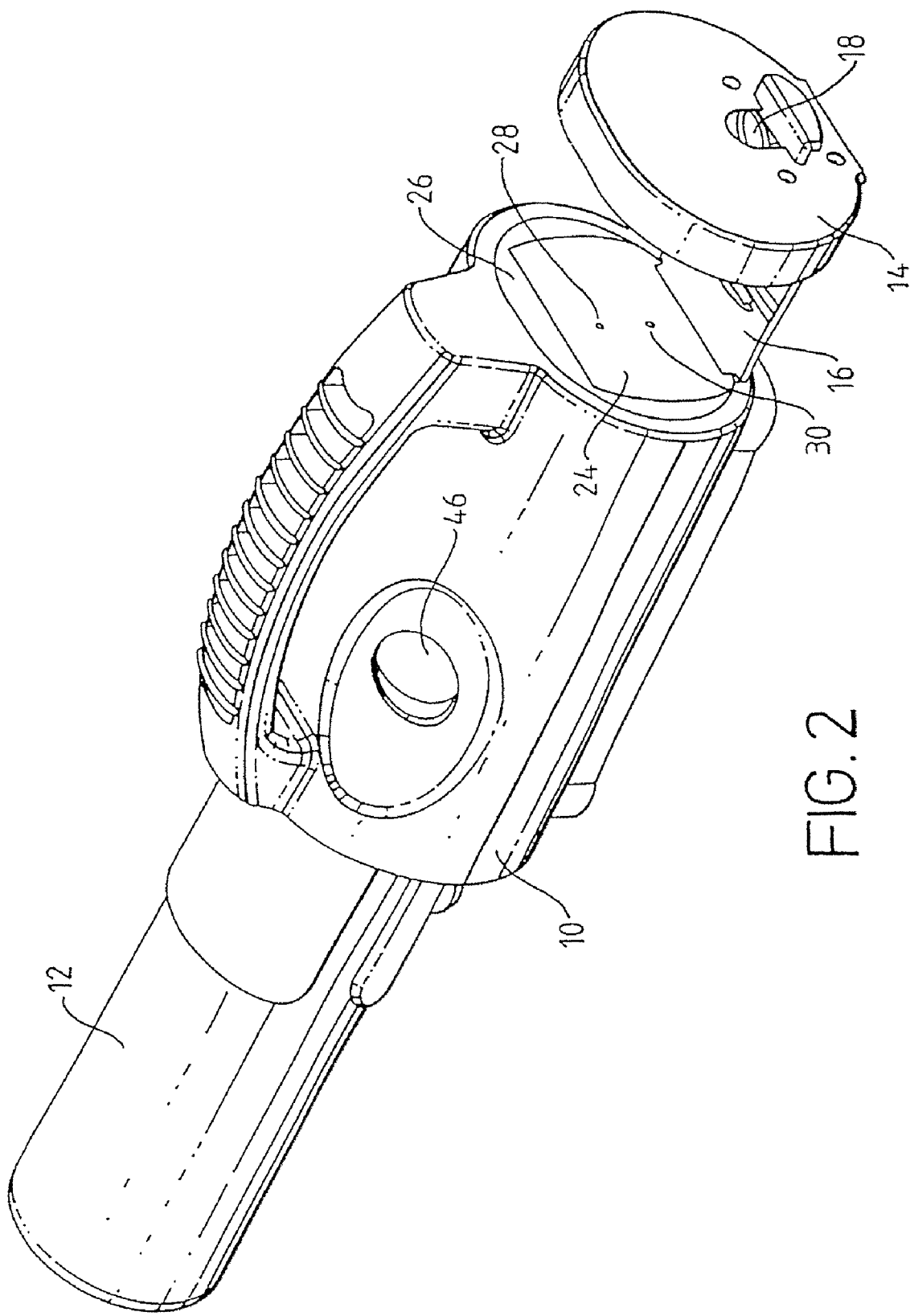
FIG. 2 *a* is perspective view of the calibration apparatus of FIG. 1 is a different configuration.
Figure 3:
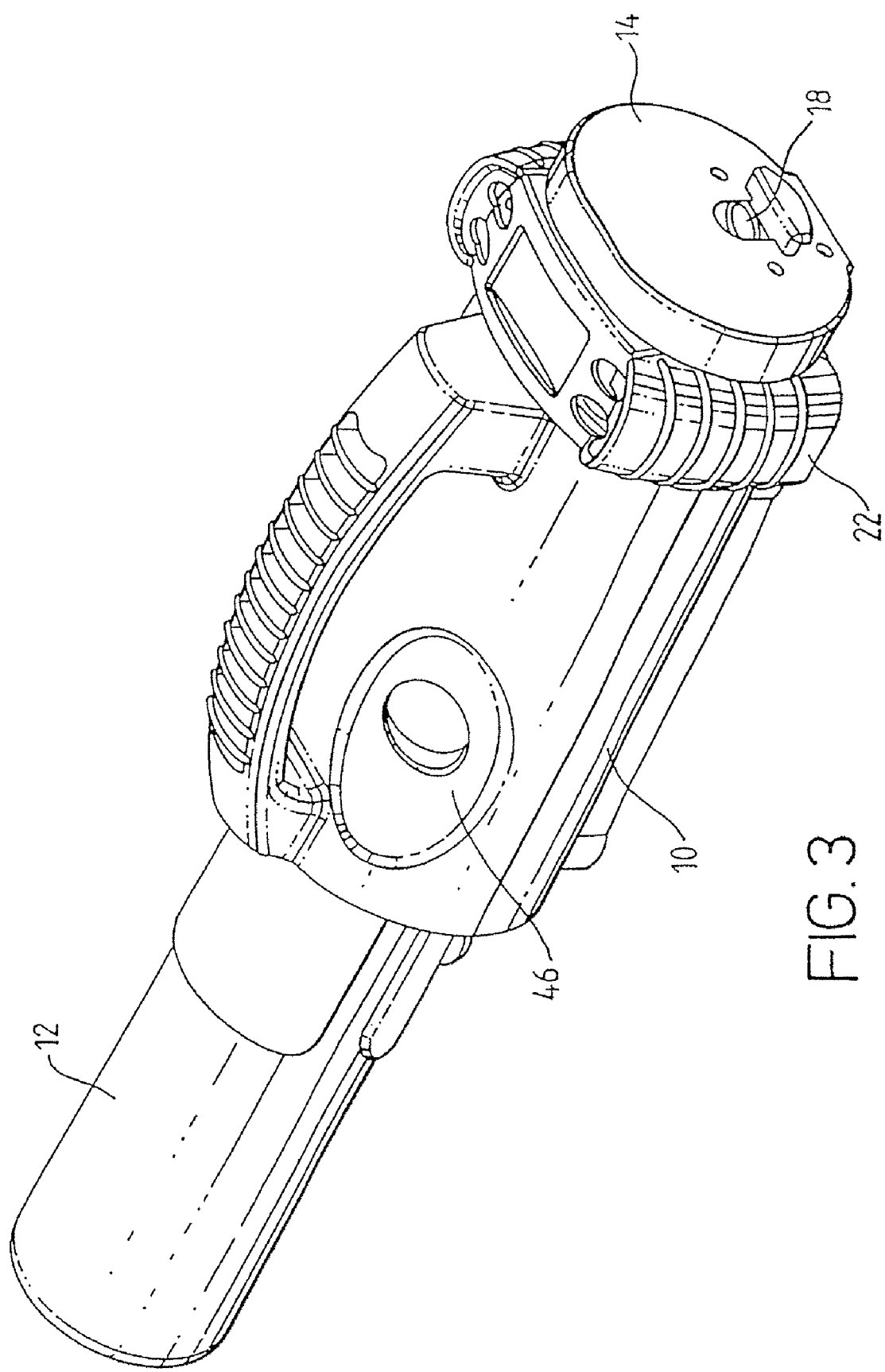
FIG. 3 is a perspective view of the calibration apparatus of FIGS. 1 and 2 together with a detector.

Referring initially to FIGS. 1 to 3, the apparatus comprises a housing 10 containing a cylinder 12 of pressurized calibration gas that holds a mixture of gas that a detector is or may be sensitive to, for example oxygen, carbon monoxide, flammable gases and hydrogen sulphide, in an inert carrier, e.g. nitrogen. The gases are present in known predetermined concentrations. The housing includes an end panel 14 that can be slid out (see FIG. 2) while still being attached to the main housing. However, it can be latched in place by means of a latching mechanism that can be released by operating a latch 18. Thus, when the end panel 14 is pulled out, it is held in the open position shown in FIG. 2. However, when the latch 18 is operated, the latching mechanism is released and the end panel is pulled by a spring 20 (see FIG. 4) towards the main housing body.

A detector 22 can be placed within the space between the main housing body 10 and the end panel 14. The detector includes a face (not shown) that contains an inlet (not shown) that, in normal detecting operation, allows gas from the atmosphere being monitored to reach the sensors within the detector 22 by diffusion. When the latch 18 is released, it is urged by the end panel 14 and the spring 20 towards the main housing 10; the end face 24 of the main housing (against which the detector is urged) is surrounded by a compliant seal 26 so that the face of the detector that contains the gas diffusion inlet (not shown) is sealed against the end face 24 of the main housing in a gas-tight manner. The end face 24 includes gas inlet port 28 and a gas outflow port 30 that will be described in greater detail in connection with FIG. 4.

Figure 4:
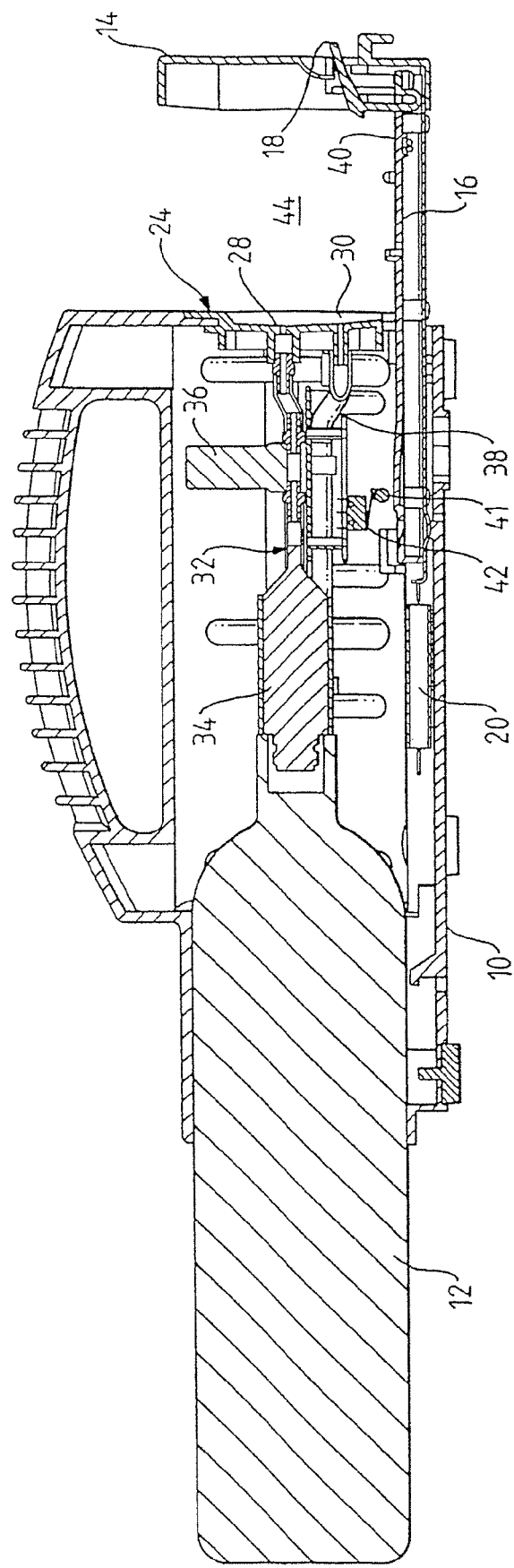
FIG. 4 is a cross-sectional view through the apparatus in the configuration shown in FIG. 2.

Referring now to FIG. 4, the gas cylinder 12 is shown connected by a known fitting to a conduit 32 containing a pressure/flow regulator 34 that produces a constant flow of calibration gas, e.g. at a rate of 0.1 liters per minute. The conduit also contains a solenoid valve 36 that opens and closes the conduit in response to an electrical signal received from a microprocessor 21 (see FIG. 5) within the detector. The conduit 32 ends in inlet port 28 described above.

In the course of calibration, gas already within the detector, e.g. air, is flushed out by the calibration gas, which passes through outlet port 30. An exhaust conduit 38 vents such gas to atmosphere or to a safe disposal arrangement.

The arm 16 also contains electrical connectors 40 (only one shown) that engage with corresponding connectors (not shown) within the detector 22. The detector 22 includes a microprocessor 21 (see FIG. 5) that controls the calibration performed by the calibration apparatus. The signals from the detector 22 are fed via connectors 40 to open and close the solenoid valve 36. A microswitch 42 is also provided having rocker 41 that closes the switch contacts when pressed upwardly by a land (not visible) on the arm 16. The land is positioned on the arm such that it presses against the rocker 41 (and hence closes the microswitch) when the distance between the end panel 14 and the face 24 corresponds to the width of the detector 22. This means that the microswitch is closed when the detector 22 is in place and pressed against end face 24 but otherwise the microswitch is open. Thus the microswitch can detect that a detector has been installed correctly within the calibration apparatus.

When the detector 22 is placed within the space 44 between the end panel 14 and end face 24 of the main housing, the latch 18 is released, thereby allowing the spring 20 to urge the end panel 14 in the left hand direct (as seen in FIG. 4), thereby pressing the detector 22 against the end face 24 of the main housing. The gas inlet of the detector (not shown), which normally allows gas from the atmosphere to diffuse into the detector to reach sensors within the detector, is sealed against the end face 24 so that a gas tight seal is formed around the detector gas inlet of the detector and the end face 24. The ports 28 and 30 are thus in fluid communication with the gas inlet of the detector. Gas supplied along the conduit 32 can thus pass into the inlet of the detector and reach the sensors within the detector. Likewise, gas flushed from the detector can be vented via port 30 to the atmosphere.

Figure 5:
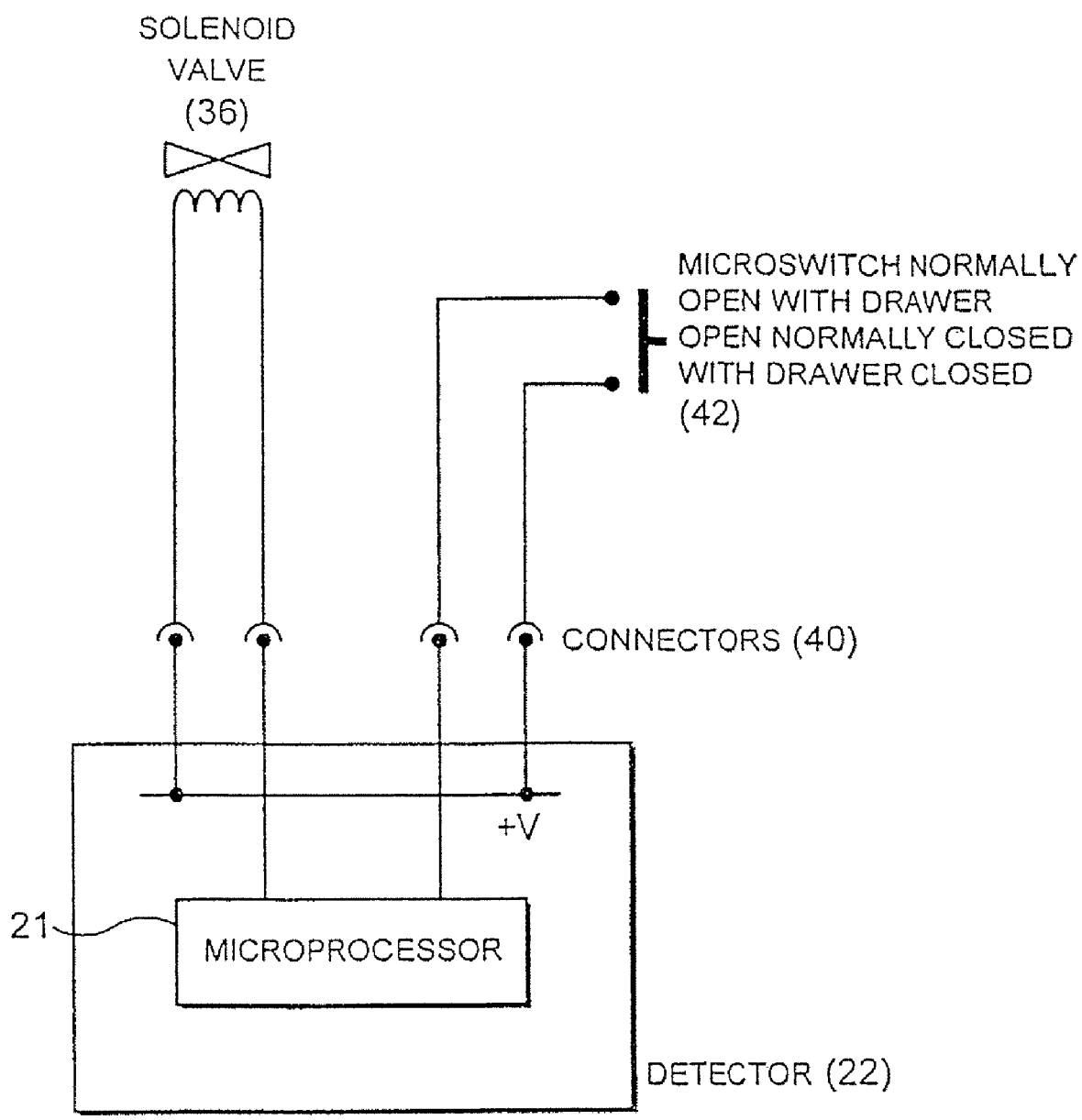
FIG. 5 is a schematic circuit diagram showing the connections between the calibration apparatus and a sensor being calibrated.

FIG. 5 shows the connections between, on the one hand, the microswitch 42 and the solenoid valve 36 and, on the other hand, the microprocessor 24 within the detector 22. When a detector has been installed within the space 44 between end panel 14 and end face 24, the microswitch is, as described above, closed which causes a positive voltage V from rail 23 to be applied via contacts 40 to the microprocessor, thereby indicating that a sensor has been properly installed within the space 44 and that the arm 16 has been retracted. The microprocessor can then pass control signals via contacts 40 to the solenoid valve 36 and take control of the calibration process. However, the user is first asked on a screen (not shown) whether he wishes a calibration cycle to be initiated. He initiates the calibration cycle by pressing a push button 46 on the main housing. Once the switch 46 is activated, the complete calibration procedure is taken over by the microprocessor 21 within the detector 22.

Figure 6:
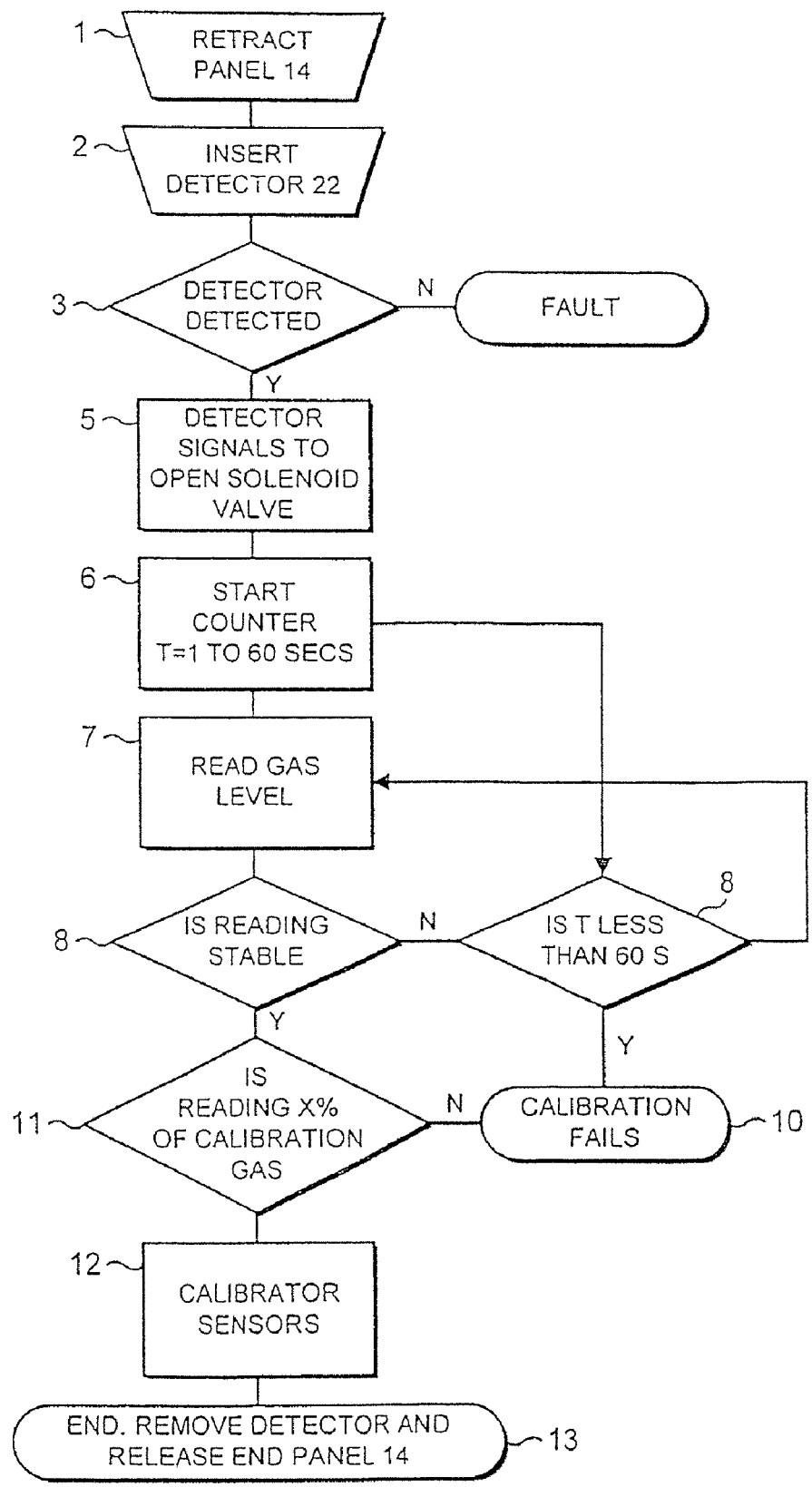
FIG. 6 is a logic diagram showing the calibration process using the apparatus of the present invention.

The calibration procedure is thus as follows (referring to FIG. 6):

1. The end panel 14 is pulled away from the main housing 10 and latched in an open position (Box 1).
2. The detector 22 is placed in the space 44 and the latch is released to urge the end panel 14 towards the main housing and hence to urge the detector against the face 24 (Box 2);
3. The microswitch 44 is closed by the land, indicating that the detector is correctly installed (Box 3); if not, an error signal is reported (Box 4);
4. Once the user has approved calibration by pressing pushbutton 46, the microprocessor 21 sends a signal via contacts 40 to the solenoid valve 36 to open the solenoid valve 36 thereby allowing calibration gas to flow from the gas cylinder 12 through the flow control valve 34, at a flow rate of approximately 0.1 liters per minute, through conduit 32 and out through port 28 into the inlet of the detector 22 (Box 5);
5. A timer within the microprocessor is started when calibration is initiated; (Box 6);
6. The sensors within the detector 22 can therefore register and respond to the gas supplied. The calibration gas contains a known fixed concentration of various gases to be detected, e.g. oxygen, carbon monoxide, hydrogen sulphide and a flammable gas, e.g. butane. Gas flushed out from within the detector 22 can escape via port 30 and conduit 38 to the atmosphere. It generally takes approximately 30 seconds to reach a steady state reading;
7. The microprocessor "reads" the signals from the sensors (Box 7). The microprocessor then performs a loop (Boxes 7, 8 and 9); if the loop is being performed for the first time or if the signal from a sensor is not the same (within predefined tolerances) as the signal on the previous iteration of the loop (Box 8), the timer is interrogated (Box 9). If the time elapsed since the initiation of the calibration is less than 60 seconds, the signal from the sensors is again read (Box 7). The loop is repeated until the signals from the sensors have reached a stable steady state reading or 60 seconds have elapsed;
8. If more than 60 seconds have elapsed and steady state readings from the sensors have not been detected, an error signal is generated and the calibration fails (Box 10);
9. If steady state readings from the sensors have not been detected within 60 seconds, the microprocessor interrogates the magnitude of the signals from the sensors (Box 11); if they fall outside predetermined ranges, an error signal is generated and the calibration fails (Box 10);
10. If the calibration has not failed, the microprocessor within the detector calibrates the sensors by adjusting the gain of the detector to produce a reading exactly corresponding to the known composition of the calibration gas (Box 12);
11. The detector 22 is then removed from the calibration apparatus (Box 13).

The error signal (Box 10) could be caused either by a malfunction of the sensor (indicating that it needs replacing) or by dirty filters within the detector 22. Thus, if an error signal is generated, the filter should first of all be cleaned or replaced and calibration re-initiated. If the detector, on recalibration, also fails, then this is indicative that one or more of the sensors should be replaced. If, after replacement of the sensors, the detector still generates an error signal, then that is indicative of a fault in the detector itself.

The faster the flow rate of calibration gas to the detector, the faster it reaches the steady state reading. Furthermore, at low flow rates of the calibration gas, the magnitude of the final steady state signal from a sensor will depend on the flow rate. However at higher flow rates (approximately 0.3 to 0.5 liters per minute or greater), the final steady state signal from a sensor will be largely independent of the flow rate. The prior art has generally used flow rates of 0.5 liters/minute and avoided using flow rates as low as 0.1 liters per minute since, if the rate of flow of calibration gas were to vary at a low flow rate, the magnitude of the steady state response signal could vary and hence would be unreliable. On the other hand, it is desirable to use as low a flow rate of gas as possible, firstly because it more closely approximates to the normal operation of a gas detector, whereby gas diffuses into the detector rather than being pumped into the detector, and secondly, the lower the rate of flow, the less calibration gas is used. We have found that, by reducing the length of the conduit 32 and by clamping the detector against the end face of the housing 10, and by providing the whole calibration equipment within a single housing, reliable readings can be obtained for calibration of a gas sensor, even at 0.1 liters per minute.

It can be seen that calibration can be completed simply and without special staff training within approximately one minute and can be undertaken by personnel prior to entering a hazardous area. Thus, the calibration can replace the inexact "testing" of the detector, which merely shows that the sensors are operating rather than that they provide accurate readings. There is no need to send the detector away for calibration or arrange for special visits by trained calibration staff. Also, the arrangement of the calibration apparatus allows the use for low flow rates of calibration gas without being affected by drafts. Accordingly, the present invention provides a cheaper and safer system for testing and calibrating gas detectors prior to entering hazardous areas.

Because the whole calibration process is controlled by the detector and not the calibration apparatus, the calibration data is held within the microprocessor and so the calibration data for each sensor is stored within the detector itself and so for example the improper functioning of a sensor can be detected and a signal generated that the sensor should be replaced. In addition, by controlling the calibration apparatus from the detector, the calibration apparatus will be relatively simple and cheap to manufacture. The detector will generally already have a microprocessor for its normal operation and so the incorporation of the software for controlling calibration and for logging calibration data into the microprocessor does not make the detector any more expensive.

The apparatus may also be made light enough for it to be portable and compact enough that it can be easily stored. Thus it can be used readily in the most convenient position for calibration.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A portable detector for monitoring a gas in an atmosphere, the detector comprising
   a housing,
   at least one gas sensor carried by the housing,
   electrical connectors externally carried by the housing for establishing electrical connections to an external calibration apparatus, and
   a microprocessor carried by the housing, wherein the portable detector is shaped so as to be slidably engagable and disengagable within the external calibration apparatus, and wherein the microprocessor initiates a flow of calibration gas from the external calibration apparatus when the electrical connectors engage with corresponding electrical connectors of the external calibration apparatus, the microprocessor calibrates the at least one gas sensor, and the microprocessor stops the flow of calibration gas from the external calibration apparatus.

2. A detector as claimed in claim 1 wherein the at least one sensor is an electrochemical gas sensor.

3. A detector as claimed in claim 1 that includes a calibration circuit carried by the housing for calibrating the output of the detector in -accord with the concentration of the gas being monitored in the calibration gas.

4. A detector as claimed in claim 1 that includes a circuit for storing calibration data, the circuit is carried by the housing.

5. A detector as claimed in claim 1 wherein the electrical connectors carried by the housing are releasably coupled to the calibration apparatus.

6. A portable detector for monitoring a gas in an atmosphere, the detector comprising:
   a housing;
   at least one gas sensor carried by the housing, the monitored gas in the atmosphere reaching the at least one gas sensor by diffusion;
   electrical connectors externally carried by the housing, the housing is shaped for slidably engaging and disengaging electrical connections to an external calibration apparatus; and
   a microprocessor carried by the housing, the microprocessor controlling a flow of calibration gas from the external calibration apparatus via signals provided from the microprocessor through the connectors to initiate and terminate the flow of calibration gas from the external calibration apparatus to the detector at a predetermined rate.

7. A detector as claimed in claim 6 wherein the portable detector is separable from the calibration apparatus to monitor an ambient atmosphere.

8. A portable detector for monitoring a gas in an atmosphere, the detector comprising:
   a housing;
   at least one gas sensor carried by the housing, the monitored gas in the atmosphere reaching the at least one gas sensor by diffusion;
   electrical connectors externally carried by the housing for establishing electrical connections to the external calibration apparatus, the portable detector is shaped so as to be slidably engagable and disengagable within the external calibration apparatus to monitor an ambient atmosphere; and
   a microprocessor carried by the housing, the microprocessor controlling a flow of calibration gas from the external calibration apparatus via signals provided from the microprocessor through the connectors to initiate and terminate the flow of calibration gas from the external calibration apparatus to the detector at a predetermined rate.

9. A detector as claimed in claim 8 wherein the electrical connectors carried by the housing are releasably coupled to the calibration apparatus.

* * * * *